US009247891B2

(12) United States Patent
Vos

(10) Patent No.: US 9,247,891 B2
(45) Date of Patent: Feb. 2, 2016

(54) PREDICTION OF CARDIAC RESYNCHRONIZATION THERAPY RESPONSE BASED ON VARIABILITY OF REPOLARIZATION

(71) Applicant: UMC Utrecht Holding B.V., Utrecht (NL)

(72) Inventor: Marc A. Vos, Utrecht (NL)

(73) Assignee: UMC Utrecht Holding B.V., Utrecht (NL)

( * ) Notice: Subject to any disclaimer, the term of this patent is extended or adjusted under 35 U.S.C. 154(b) by 0 days.

(21) Appl. No.: 14/159,010

(22) Filed: Jan. 20, 2014

(65) Prior Publication Data

US 2015/0201857 A1   Jul. 23, 2015

(51) Int. Cl.
| | | |
|---|---|---|
| *A61B 18/18* | (2006.01) | |
| *A61B 5/04* | (2006.01) | |
| *A61B 5/0402* | (2006.01) | |
| *A61B 5/00* | (2006.01) | |
| *A61B 5/0432* | (2006.01) | |
| *A61B 5/0452* | (2006.01) | |
| *A61B 5/02* | (2006.01) | |
| *A61N 1/362* | (2006.01) | |
| *A61N 1/368* | (2006.01) | |
| *G06F 19/00* | (2011.01) | |

(52) U.S. Cl.
CPC .......... *A61B 5/04012* (2013.01); *A61B 5/0402* (2013.01); *A61B 5/0432* (2013.01); *A61B 5/0452* (2013.01); *A61B 5/7264* (2013.01); *A61B 5/02028* (2013.01); *A61N 1/3627* (2013.01); *A61N 1/3684* (2013.01); *G06F 19/3481* (2013.01)

(58) Field of Classification Search
USPC ......................................................... 600/519
See application file for complete search history.

(56) References Cited

U.S. PATENT DOCUMENTS

| | | | |
|---|---|---|---|
| 5,560,368 | A | 10/1996 | Berger |
| 7,107,093 | B2 | 9/2006 | Burnes |
| 7,215,998 | B2 | 5/2007 | Wesselink et al. |
| 7,672,716 | B1 | 3/2010 | Koh |
| 7,912,544 | B1 | 3/2011 | Min et al. |
| 2004/0044374 | A1 | 3/2004 | Weinberg et al. |
| 2005/0038478 | A1 | 2/2005 | Klepfer et al. |
| 2005/0043764 | A1 | 2/2005 | Wesselink et al. |
| 2005/0234356 | A1* | 10/2005 | Rowlandson et al. ........ 600/510 |

(Continued)

OTHER PUBLICATIONS

Timineri et al., "Selection of patient for cardiac resynchronization therapy: role of QT corrected dispersion," Pace, Jul. 2012; 35(7):850-855.

(Continued)

*Primary Examiner* — Nicole F Lavert
(74) *Attorney, Agent, or Firm* — Shumaker & Sieffert, P.A.

(57) ABSTRACT

Techniques for determining whether a patient will respond to cardiac resynchronization therapy (CRT) include identifying a plurality of consecutive cardiac beats within a cardiac electrogram of the patient and, for each of the consecutive cardiac beats, measuring a repolarization interval. The techniques also include determining a variability of the measured repolarization intervals. The variability of the measured repolarization intervals indicates whether the patient will respond to CRT. For example, a variability lower than a predetermined threshold may indicate that the patient is a CRT responder, while a variability greater than the predetermined threshold may indicate that the patient is a CRT non-responder.

23 Claims, 8 Drawing Sheets

(56) References Cited

U.S. PATENT DOCUMENTS

| | | | |
|---|---|---|---|
| 2006/0281997 A1* | 12/2006 | Guerrero | 600/509 |
| 2008/0021336 A1 | 1/2008 | Dobak, III | |
| 2010/0113889 A1* | 5/2010 | Ghanem | 600/301 |
| 2011/0190650 A1 | 8/2011 | McNair | |
| 2011/0251504 A1 | 10/2011 | Tereshchenko et al. | |
| 2013/0035738 A1 | 2/2013 | Karst et al. | |

OTHER PUBLICATIONS

Hsing et al., "Paced left ventricular QRS width and ECG parameters predict outcomes after cardiac resynchronization therapy," Prospect-ECG substudy. Circ Arrhythm Electrophysiol, Dec. 2011; 4(6):851-857.

Varkevisser et al.,"Beat-to-beat variability of repolarization as a new biomarker for proarrhythmia in vivo," Heart Rhythm, Oct. 2012; 9(10):1718-1726.

Chao, et al., "An intelligent classifier for prognosis of cardiac resynchronization therapy based on speckle-tracking echocardiograms," Artificial Intelligence in Medicine, vol. 54, Mar. 2012, pp. 181-188.

Dobson, et al., "QT Variability Index," Progress in Cardiovascular Diseases, vol. 56, Sep. 2013, pp. 186-194.

Figueredo, et al., "Usefulness of Beat-to-Beat QT Dispersion Fluctuation for Identifying Patients with Coronary Heart Disease at Risk for Ventricular Arrhythmias," The American Journal of Cardiology, Jan. 2001, pp. 1235-1239.

Hina, et al., "Association of corrected QT dispersion with symptoms improvement in patients receiving cardiac resynchronization therapy," Heart Vessels, vol. 23, Sep. 2008, pp. 325-333.

Hinterseer, et al., "Usefulness of Short-Term Variability of QT Intervals as a Predictor for Electrical Remodeling and Proarrhythmia in Patients with Nonischemic Heart Failure," The American Journal of Cardiology, vol. 106, No. 2, Jul. 15, 2010, pp. 216-220.

Piccirillo, et al., "Influence of aging and chronic heart failure on temporal dispersion of myocardial repolarization," Clinical Interventions in Aging, Mar. 2013, pp. 293-300.

Tereshchenko, et al., "Strong coherence between heart rate variability and intracardiac repolarization lability during biventricular pacing is associated with reverse electrical remolding of the native conduction and improved outcome," Journal of Electrocardiology, vol. 44, No. 6, Jan. 2011, pp. 713-717.

Tereshchenko, et al., "Towards a better understanding of QT interval variability," Therapeutic Advances in Drug Safety, vol. 2, No. 6, Dec. 2011, pp. 245-251.

International Search Report and Written Opinion from International Application No. PCT/EP2015/050860, dated Apr. 17, 2015, 15 pp.

Response to Written Opinion dated Apr. 17, 2015, from counterpart International Application No. PCT/ EP2015/050860, filed on Nov. 13, 2015, 6 pages.

* cited by examiner

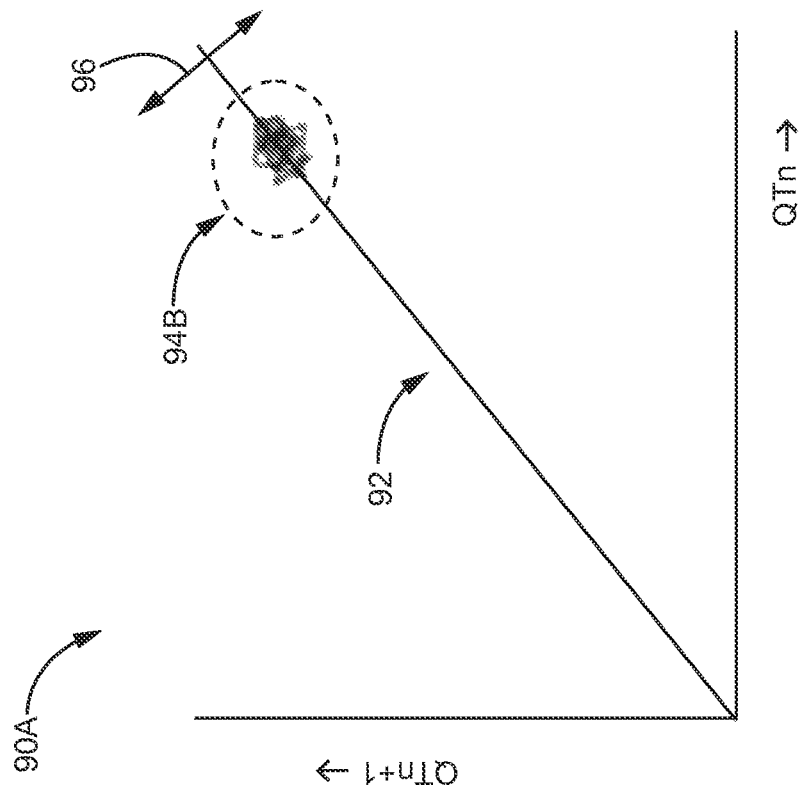
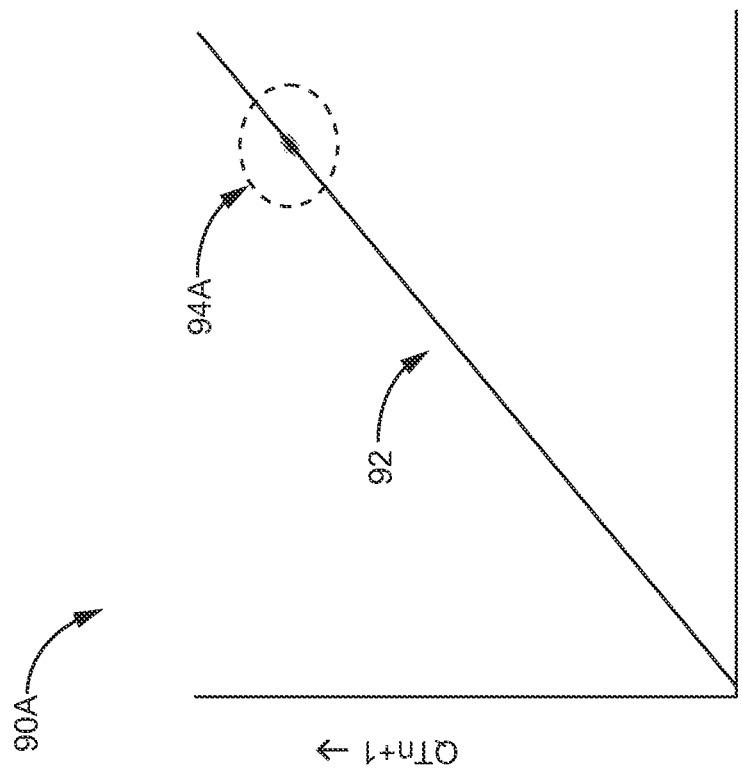

PREDICTION OF CARDIAC RESYNCHRONIZATION THERAPY RESPONSE BASED ON VARIABILITY OF REPOLARIZATION

TECHNICAL FIELD

The invention relates to cardiac monitoring and therapy and, more particularly to cardiac resynchronization therapy (CRT).

BACKGROUND

Cardiac pacing is delivered to patients to treat a wide variety of cardiac dysfunctions. Cardiac pacing is often delivered by an implantable medical device (IMD), which may also provide cardioversion or defibrillation in response to detected cardiac tachyarrhythmias, if needed. The IMD delivers such stimulation to the heart via electrodes located on one or more leads, which are typically intracardiac leads.

Patients with heart failure may be treated with cardiac resynchronization therapy (CRT). CRT is a form of cardiac pacing. The ventricles of some heart failure patients contract in an uncoordinated, or asynchronous, manner, which greatly reduces the pumping efficiency of the ventricles. CRT delivers pacing pulses at particular times, e.g., atrio-ventricular (A-V) intervals and/or intra-ventricular (V-V) intervals, and particular locations, e.g., to one or both of the right and left ventricles, to re-coordinate the contraction of the ventricles. In some examples, CRT involves delivery of pacing pulses to both ventricles to synchronize their contraction. In other examples, CRT involves delivery of pacing pulses to one ventricle, such as the left ventricle, to synchronize its contraction with that of the right.

Numerous trials have shown the benefit of CRT over other, e.g., pharmacological, therapies. However, some patients that meet the guidelines for implantation of an IMD to provide CRT, ultimately do not respond to the provided CRT, e.g., do not show significant improvement of cardiac function when CRT is delivered.

SUMMARY

In general, this disclosure is directed to techniques for determining whether a patient will respond, e.g., is likely to respond or has a relatively high likelihood of responding, to CRT. More particularly, the disclosure is directed toward techniques for determining whether a patient will respond to CRT based on the variability, e.g., short-term variability, of the timing of repolarization of the heart of the patient. The techniques of this disclosure may provide a relatively simple, non-invasive measurement that may accurately distinguish between patients who will likely respond to CRT, and those who will likely not respond to CRT.

In some examples, a system implementing the techniques of this disclosure identifies a plurality of consecutive cardiac beats within a cardiac electrogram, e.g., a digital cardiac electrogram, of a patient. The cardiac electrogram may be a non-invasive electrocardiogram (ECG), such as a twelve-lead ECG. For each of the consecutive cardiac beats, the system measures a repolarization interval, such as a QT interval. The system determines a variability of the measured repolarization intervals. For example, the system may determine a short-term, beat-to-beat variability of the QT intervals (STVQT), or other repolarization intervals.

The variability of the measured repolarization intervals indicates whether the patient will respond to CRT. For example, a variability less than a predetermined threshold may indicate that the patient is more likely a CRT responder, while a variability greater than the predetermined threshold may indicate that the patient is more likely a CRT non-responder. In this manner, a system implementing the techniques of this disclosure may indicate whether a particular patient will respond to CRT based on an analysis of the short-term variability of repolarization of the heart of the patient.

In one example, a system for determining whether a patient will respond to cardiac resynchronization therapy (CRT) comprises an acquisition module configured to acquire a cardiac electrogram of the patient. The system further comprises an analysis module configured to identify a plurality of consecutive cardiac beats within the cardiac electrogram, for each of the consecutive cardiac beats, measure a repolarization interval, and determine a variability of the measured repolarization intervals. The variability of the measured repolarization intervals indicates a likelihood that the patient will respond to CRT.

In another example, a method for determining whether a patient will respond to cardiac resynchronization therapy (CRT) comprises acquiring a cardiac electrogram of the patient, and identifying a plurality of consecutive cardiac beats within the cardiac electrogram. The method further comprises, for each of the consecutive cardiac beats, measuring a repolarization interval, and determining a variability of the measured repolarization intervals. The variability of the measured repolarization intervals indicates a likelihood that the patient will respond to CRT.

In another example, a system for determining whether a patient will respond to cardiac resynchronization therapy (CRT) comprises means for acquiring a cardiac electrogram of the patient, and means for identifying a plurality of consecutive cardiac beats within the cardiac electrogram. The system further comprises, for each of the consecutive cardiac beats, means for measuring a repolarization interval, and means for determining a variability of the measured repolarization intervals. The variability of the measured repolarization intervals indicates a likelihood that the patient will respond to CRT.

In another example, a computer-readable storage medium comprises program instructions that, when executed by one or more processors of a system for determining whether a patient will respond to cardiac resynchronization therapy (CRT), cause the processors to acquire a cardiac electrogram of the patient, and identify a plurality of consecutive cardiac beats within the cardiac electrogram. The instructions further cause the one or more processors to, for each of the consecutive cardiac beats, measure a repolarization interval, and determine a variability of the measured repolarization intervals. The variability of the measured repolarization intervals indicates a likelihood that the patient will respond to CRT.

The details of one or more examples are set forth in the accompanying drawings and the description below. Other features, objects, and advantages will be apparent from the description and drawings, and from the claims.

BRIEF DESCRIPTION OF DRAWINGS

FIGS. 4A and 4B are example Poincare plots illustrating variability of repolarization intervals.

DETAILED DESCRIPTION

As discussed above, CRT is a form of cardiac pacing delivered to one or both of the right and left ventricles to re-synchronize or re-coordinate the mechanical contractions of the ventricles, i.e., so that the contractions of the left and right ventricles are coordinated or synchronized with each other. In some examples, CRT includes, and may be referred to, as bi-ventricular (Bi-V) pacing.

In some examples, an implantable medical device (IMD) that delivers CRT is coupled to three leads that connect the IMD to electrodes located in or near the right atrium, right ventricle and left ventricle, respectively. The IMD senses atrial and ventricular depolarizations, and delivers CRT pacing pulses to one or both ventricles, and in some cases an atrium, via the electrodes. The delivery of CRT pacing pulses to one or both ventricles by the IMD may be controlled by programmed atrio-ventricular (A-V) intervals and/or intra-ventricular (V-V) intervals. Such intervals may begin on a paced or sensed atrial or ventricular depolarization.

As discussed above, some patients that meet the guidelines for implantation of an IMD to provide CRT ultimately do not respond to the provided CRT. A patient that does not respond to CRT does not show significant improvement of cardiac function when CRT is delivered. Metrics of cardiac function that should improve if a patient is a responder to CRT include, for example, left-ventricular end systolic volume (LVESV), left-ventricular end diastolic volume (LVEDV) and left-ventricular ejection fraction (LVEF).

This disclosure describes techniques for determining whether a patient will respond, e.g., is likely to respond or has a relatively high likelihood of responding, to CRT prior to implantation of an IMD to provide CRT. More particularly, this disclosure describes techniques for determining whether a patient will respond to CRT based on the variability, e.g., short-term, beat-to-beat variability, of the timing of repolarization of the heart of the patient. Relatively lower repolarization variability may indicate that the patient will more likely respond to CRT, while relatively higher repolarization variability may indicate that the patient will more likely not respond to CRT. The techniques of this disclosure may provide a relatively simple, non-invasive measurement that may accurately distinguish between patients who will respond to CRT, and those who will not respond to CRT.

Figure 1A:
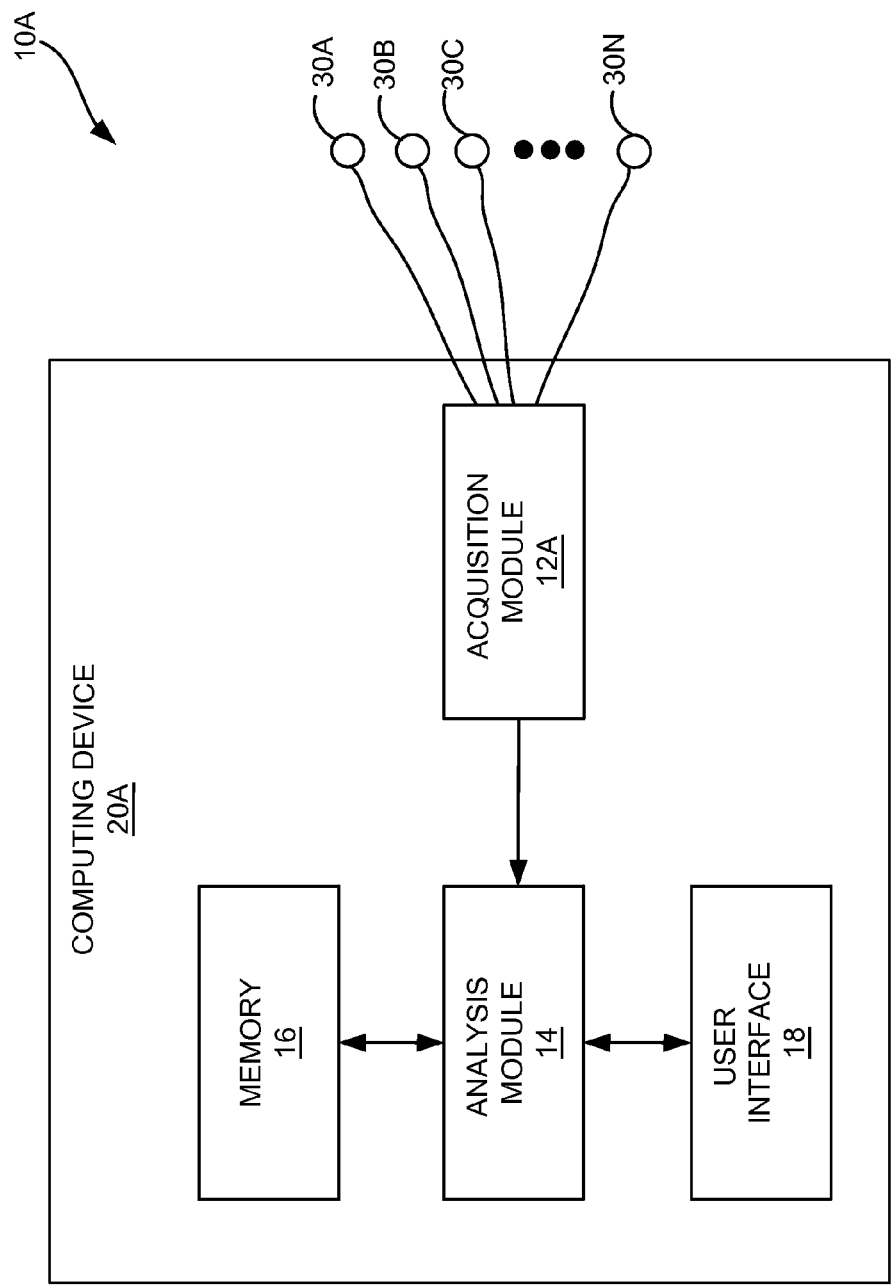
FIGS. 1A and 1B are block diagrams illustrating example systems for determining whether a patient will respond to CRT in accordance with the techniques of this disclosure.
Figure 1B:
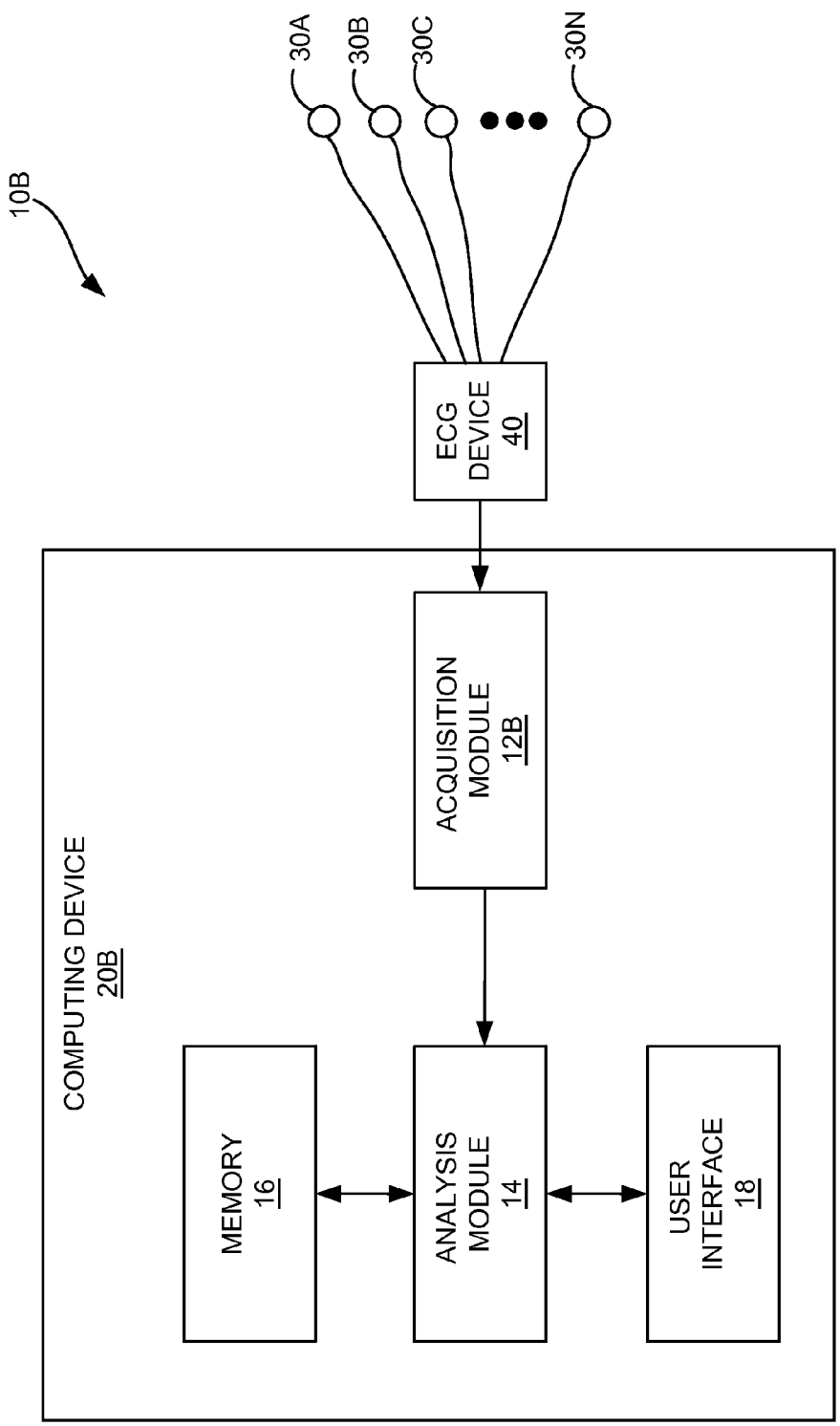

FIGS. 1A and 1B are block diagrams illustrating example systems 10A and 10B (collectively "systems 10") for determining whether a patient will respond to CRT in accordance with the techniques of this disclosure. System 10A of FIG. 1A includes a computing device 20A. Computing device 20A includes an acquisition module 12A, analysis module 14, memory 16 and user interface 18.

Computing device 20A and, more particularly, acquisition module 12A, is coupled to a plurality of electrodes 30A-30N (collectively "electrodes 30"). Electrodes 30 may be included as part of pads or patches configured to be attached, e.g., by an adhesive, to the surface, e.g. skin, of a patient (not shown). Electrodes 30 may be attached to the surface of a patient, and configured to sense a cardiac electrogram, e.g., an electrocardiogram (ECG) or other digital cardiac electrogram, of the patient. For example, electrodes may be attached to the patient at locations suitable for sensing a twelve-lead ECG of the patient, e.g., electrodes 30 may be attached to respective limbs or the torso of the patient.

Acquisition module 12A is configured to acquire an ECG, e.g., twelve lead ECG, of the patient based on the signals received from electrodes 30. Accordingly, acquisition module 12A may include circuitry and be configured as is known in the art for ECG acquisition devices. For example, acquisition module 12A may include circuitry for amplifying and filtering the signals received from electrodes 30. Acquisition module 12A may also include circuitry configured to generate an ECG signal, e.g., twelve-lead ECG signal, based on the signals received from a plurality of vectors formed by two or more of electrodes. Additionally, acquisition module 12A may include analog-to-digital conversion circuitry for converting the analog ECG signal to a digital ECG signal. Acquisition module 12A may comprise a digital signal processor (DSP).

Analysis module 14 receives the ECG, e.g., digital ECG, from acquisition module 12A. Analysis module 14 comprises one or more processors, such as one or more microprocessors, DSPs, application specific integrated circuits (ASIC's), field-programmable gate arrays (FPGAs), analog processing circuitry, or the like. Memory 16 may store program instructions that, when executed by the one or more processors of analysis module 14, cause the analysis module and systems 10 to perform the techniques for determining whether a patient will respond to CRT described herein. Memory 16 may include any of various types of volatile or non-volatile media, such as random access memory (RAM), read-only memory (ROM), non-volatile RAM (NVRAM), electronically-erasable programmable ROM (EEPROM), flash memory, a hard drive, removable media (e.g., removable flash or CD-ROM), or the like. Memory 16 may also store ECGs acquired by acquisition module 12A, one or more repolarization interval variability threshold values, data indicating whether one or more patients will respond to CRT, or any other values or data used or generated by analysis module 14 when determining whether a patient is relatively likely to respond to CRT according to the techniques described herein.

User interface 18 may comprise an input interface and/or an output interface. For example, user interface 18 may comprises any one or more of a display, speaker, pointing device, keyboard, or touchscreen. User interface 18 may be configured to display ECGs, repolarization interval information, repolarization interval variability information, and/or indications of whether one or more patients will respond to CRT. User interface 18 may be configured to receive any user input that facilitates the techniques for determining whether a patient will respond to CRT described herein.

In the example system 10A of FIG. 1A, computing device 20A is electrically connected to external, patient-surface electrodes 30, and includes an acquisition module 12A configured to acquire a cardiac electrogram, e.g., ECG, from electrodes 30. In such examples, computing device 20A may take the form of an ECG device that includes analysis module 14 configured to provide the functionality described herein for determining whether a patient will respond to CRT. However, the techniques described herein for determining whether a patient will respond to CRT are not limited to such a computing device 20A or system 10A.

FIG. 1B illustrates another example system 10B. System 10B includes a computing device 20B, which includes an acquisition module 12B, analysis module 14, memory 16 and user interface 18. System 10B also includes an ECG device 40.

ECG device 40 is electrically connected to electrodes 30. ECG device 40 includes circuitry configured to acquire or generate an ECG, e.g., twelve lead ECG, of the patient based on the signals received from electrodes 30, such as the circuitry described above with respect to acquisition module 12A. Accordingly, ECG device 40 may include circuitry for amplifying and filtering the signals received from electrodes 30, circuitry configured to generate an ECG signal, e.g., twelve-lead ECG signal, based on the signals received from a plurality of vectors formed by two or more of electrodes 30, and analog-to-digital conversion circuitry for converting the analog ECG signal to a digital ECG signal.

In the example system 10B, ECG device 40 provides the ECG to acquisition module 12B of computing device 20B. Acquisition module 12B may comprise a network interface to receive the ECG from ECG device 40 via a wired and/or wireless network. In some examples, acquisition module 12B comprises an interface to receive a removable storage medium, e.g., flash or CD-ROM, and read the ECG from the medium. In either case, analysis module 14 receives the ECG from acquisition module 12B. Analysis module 14, memory 16 and user interface 18 may be the same, and configured to provide functionality, as described above with respect to system 10A of FIG. 1A.

As illustrated by FIGS. 1A and 1B, a system 10 for determining whether a patient will respond to CRT in accordance with the techniques of this disclosure may include a computing device 10A electrically connected to electrodes 30, and configured to acquire an ECG via the electrodes, or a computing device 10B configured to acquire an ECG from a separate ECG device 40. Although illustrated as being included in a single computing device 20 in the examples of FIGS. 1A and 1B, acquisition module 12, analysis module 14, memory 16 and user interface 18 may individually and/or collectively be implemented in any number of physical devices configured to communicate with each other, which may, but need not be, co-located.

Additionally, although one example of a cardiac electrogram that is analyzed to determine whether a patient will respond to CRT is an ECG acquired from external, patient-surface electrodes, other cardiac electrograms may be similarly analyzed according to the techniques of this disclosure. In some examples, a system 10 includes an IMD within the patient, which acquires a cardiac electrogram from within the patient. In some examples, the IMD is coupled to intracardiac or epicardial electrodes via one or more leads. In some examples, a housing of the IMD includes one or more electrodes. In such examples, the IMD may be implanted on or within the heart, or subcutaneously at another location within the patient. In some examples, a computing device 20 may receive the cardiac electrogram, e.g., via radio-frequency telemetry, from the IMD. In other examples, the cardiac electrogram comprises action potentials sensed by one or more electrodes of a catheter, e.g., an electrophysiology catheter, within or on the heart. In such examples, an acquisition module 12A may be electrically connected to the catheter to receive the action potentials, or an acquisition module 12B may receive the action potentials from an electrophysiology device coupled to the catheter.

Figure 2:
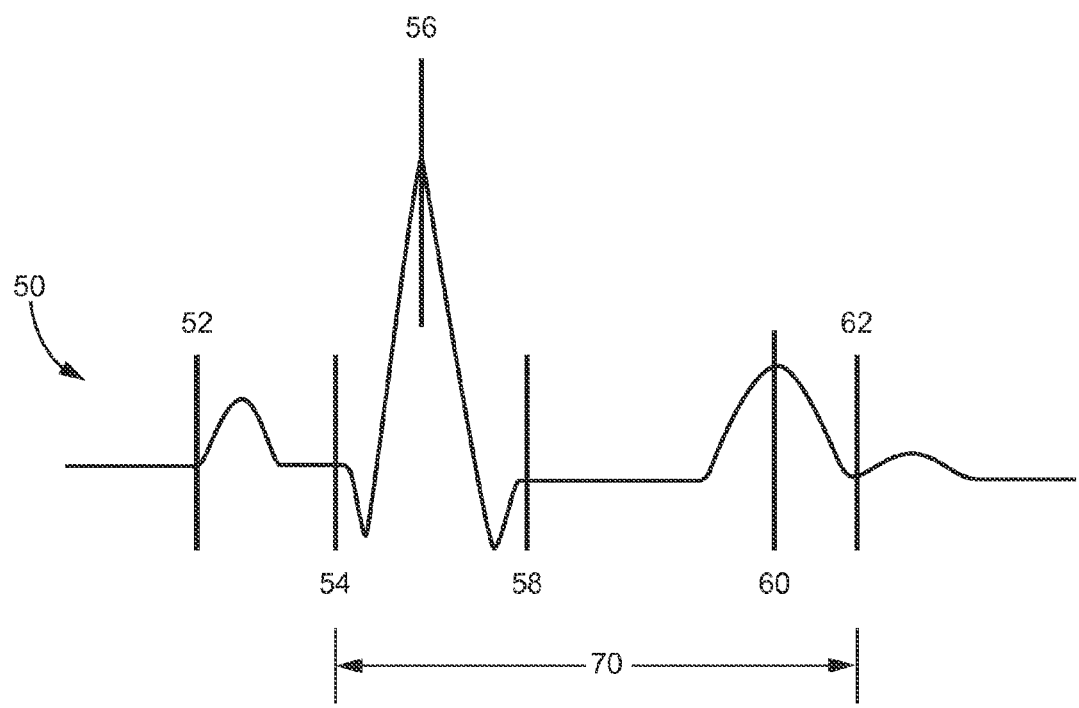
FIG. 2 is timing diagram illustrating an example beat of a cardiac electrogram signal, including an example repolarization interval.

FIG. 2 is timing diagram illustrating an example beat 50 of a cardiac electrogram signal, e.g., ECG. Beat 50 includes a single cardiac cycle, including an atrial depolarization and repolarization, and a ventricular depolarization and repolarization. A number of fiducial points or features, which occur in the cardiac electrogram during each beat or cardiac cycle, are labeled on beat 50. For example, beat 50 includes the onset of the P-wave 52, onset of the Q-wave 54, peak of the R-wave 56, end of the S-wave 58, peak of the T-wave 60, and end of the T-wave 62. Other fiducial points within each beat 50 of a cardiac electrogram include the peak of the Q-wave or onset of the R-wave, the peak of the S-wave or end of the R-wave, and the onset of the T-wave.

FIG. 2 also illustrates an example repolarization interval 70. In particular, repolarization interval 70 illustrated in FIG. 2 is a QT interval, i.e., an interval between a fiducial point or feature of the Q-wave and a fiducial point of the T-wave. Repolarization interval 70 may also be referred to as an activation-recovery interval (ARI), i.e., an interval between activation or depolarization of the heart, and recovery or repolarization of the heart.

Analysis module 14 (FIGS. 1A and 1B) measures repolarization intervals 70 for each of a plurality of consecutive beats 50. In order to measure a repolarization interval 70, analysis module 14 may identify a fiducial point or feature of the cardiac electrogram associated with activation or depolarization, e.g., a fiducial feature of the QRS complex. For example, analysis module 14 may identify a positive or negative peak of a (or positive peak of the rectified) cardiac electrogram signal, a maximum or minimum of a (or maximum of the rectified) derivative or slope of the cardiac electrogram signal, or a crossing of a threshold or zero-crossing in either the cardiac electrogram signal or its derivative. Similarly, analysis module 14 identifies a fiducial feature of the cardiac electrogram associated with recovery or repolarization. Analysis module 14 then determines the interval, e.g., time, between the fiducial feature associated with activation or depolarization, and the fiducial feature associated with recovery or repolarization, as the repolarization interval 70. In the example of FIG. 2, the fiducial feature associated with activation or depolarization is the onset of the Q-wave, but may be any fiducial feature of the QRS complex. In the example of FIG. 2, the fiducial feature associated with recovery or repolarization is the end of the T-wave, but may be any fiducial point feature, e.g., onset, peak or end, of the T-wave.

In other examples, analysis module 14 determines repolarization intervals 70 for each of a plurality of consecutive beats 50 as an interval between a point common to the plurality of beats, and a fiducial feature or point associated with repolarization, e.g., of the T-wave, for the beat. For example, analysis module 14 may align the plurality of consecutive beats 50 with each other. The alignment may be automatic, or semi-automatic, e.g., directed by user input via user interface 18. In some examples, analysis module 14 aligns a fiducial feature in each of the plurality of consecutive beats 50 with each other, to align the beats. The fiducial feature for alignment of the beats may be, for example, a peak of the R-wave 56 for each of the beats.

With the plurality of consecutive beats 50 so aligned, analysis module 14 identifies a reference point common to the plurality of beats 50. More particularly, the reference point may be derived from the points in each of beats 50 identified as the fiducial feature associated with repolarization, e.g., the peak 60 or end 62 of the T-wave in each of the plurality of beats. As examples, the common reference point may be the location of the fiducial feature in the first (earliest recorded), or any other predetermined one of the plurality of beats 50, the earliest occurrence of the fiducial feature across the plurality of beats 50 (e.g., the location or time of occurrence of the fiducial feature in the beat 50 in which the fiducial feature occurred earliest in the cardiac cycle), or a mean or median of the locations within the respective beats at which the fiducial feature occurred. For each of the plurality of consecutive beats 50, analysis module 14 measures the repolarization interval 70 for the beat as the interval (time) between the occurrence of the common reference point and the fiducial feature in that beat. In other words, the common reference point occurs at a common time in each of the plurality of beats, while the fiducial feature, e.g., end of T-wave, may occur at different times in each of the plurality of beats.

Figure 3:
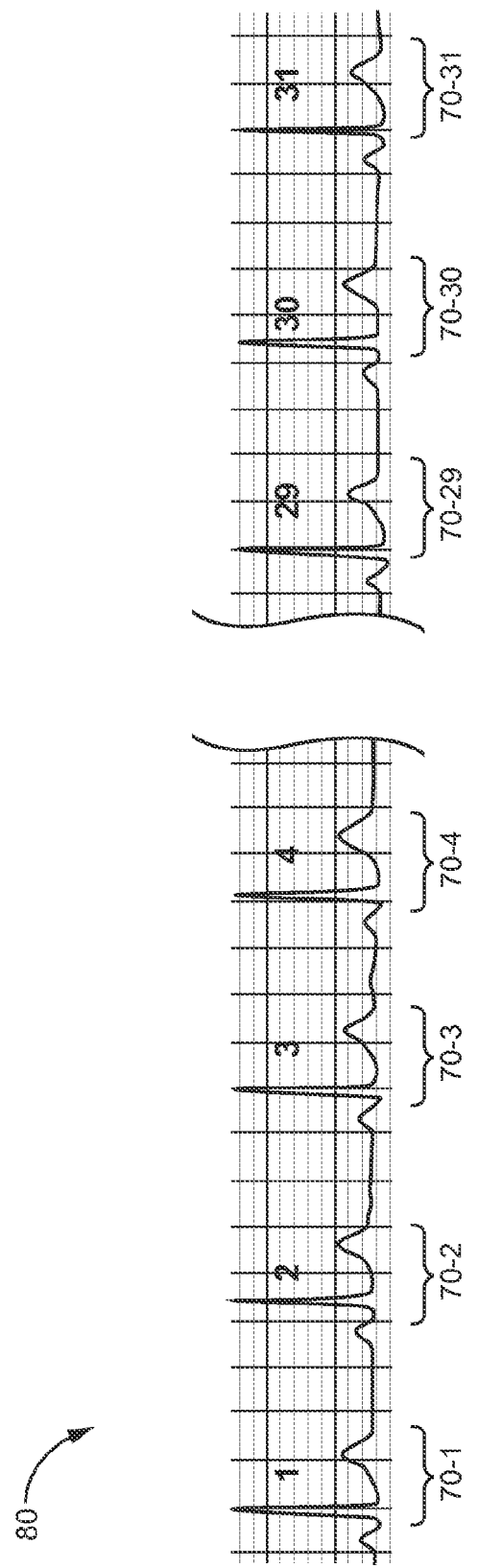
FIG. 3 is a timing diagram illustrating an example cardiac electrogram signal including a plurality of consecutive beats.

FIG. 3 is a timing diagram illustrating an example cardiac electrogram signal 80, e.g., twelve-lead ECG signal, including a thirty-one consecutive beats 50 (labeled 1-31 in FIG. 3). FIG. 3 also illustrates the repolarization intervals 70-1-70-31 of the thirty-one consecutive beats.

Acquisition module 12 acquires cardiac electrogram signal 80. In some examples, analysis module 14 analyzes the beats of cardiac electrogram signal 80 to identify any beats to discard, e.g., due to premature atrial or ventricular contraction, or insufficient signal quality. After discarding any beats, analysis module 14 identifies a sufficient number consecutive beats within the cardiac electrogram signal for determining the variability of the repolarization intervals and determining whether the patient will likely respond to CRT. In some examples, acquisition module 12 acquires a cardiac electrogram signal of sufficient length to include between approximately ten and approximately one-hundred consecutive beats, between approximately twenty and approximately fifty consecutive beats, or approximately thirty-one consecutive beats, as illustrated in FIG. 3.

If a sufficient number of consecutive beats is not found, analysis module 14 may discard the cardiac electrogram signal, and acquisition module 12 may acquire a new cardiac electrogram signal. The cardiac electrogram signal acquired by acquisition module 12 may be between approximately one minute and five minutes long, such as approximately two minutes long. In some examples, the cardiac electrogram signal acquired by acquisition module is a digital, twelve-lead ECG signal sampled at a frequency of approximately 1200 Hz.

Analysis module 14 measures repolarization intervals 70 for each of the plurality of consecutive beats 50, as discussed above. Analysis module 14 also determines the variability, e.g., short-term or beat-to-beat variability, of the repolarization intervals. In general, patients who will respond to CRT have a lower variability of repolarization intervals than patients who will not respond to CRT. Accordingly, the greater the variability of repolarization, the less likely the patient will respond to CRT, and conversely, the less the variability of repolarization, the more likely the patient will respond to CRT.

In some examples, analysis module 14 determines the variability of the repolarization intervals according to the following equation (1), where $D_n$ is the repolarization interval of the current beat, $D_{n+1}$ is the repolarization interval of the next beat, and the constant 30 is due to there being thirty-one consecutive beats in this example.

$$STV = \Sigma |D_{n+1} - D_n|/[30 \times \sqrt{2}] \quad (1)$$

In other examples, analysis module 14 determines the variability of the repolarization intervals of the consecutive beats using any of a variety of techniques for determining variability, e.g., short-term variability, of a set of values. For example, analysis module 14 may determine the variability of the repolarization intervals by using Poincare plot techniques, as described in greater detail below.

FIGS. 4A and 4B are example Poincare plots 90A and 90B (collectively "Poincare plots 90") illustrating variability of repolarization intervals 70 (FIGS. 2 and 3). In the example Poincare plots 90 of FIGS. 4A and 4B, repolarization intervals 70 are QT intervals. Poincare plot 90A of FIG. 4A illustrates variability of repolarization intervals 70 of a patient that is a CRT responder. Poincare plot 90B of FIG. 4B illustrates variability of repolarization intervals 70 of a patient that is a CRT non-responder. Poincare plots 90 illustrate that CRT non-responders have greater variability of repolarization intervals that CRT responders.

Analysis module 14 may generate Poincare plots 90 by, for each beat "n," plotting a point with an x-coordinate that is the variability value of the beat, e.g., $QT_n$, and a y-coordinate that is the variability value of the next beat, e.g., $QT_{n+1}$. Each of Poincare plots 90 includes a line 92 with a slope of one. Poincare plots 90A and 90B respectively include an area 94A and 94B (collectively "areas 94") in which the points are plotted. As illustrated in FIGS. 4A and 4B, due to the greater variability of repolarization intervals for the CRT non-responder relative to the CRT responder, the dispersion of plotted points in area 94B is greater than in area 94A.

The long-term variability of the repolarization intervals is reflected in the dispersion of the plotted points along the direction of line 92. The short-term variability of the repolarization intervals is reflected in the dispersion of the plotted points along the direction transverse to line 92, i.e., along the direction of line 96 shown in FIG. 4B. In some examples, analysis module 14 determines the short-term or beat-to-beat variability of the consecutive repolarization intervals based on the dispersion of points plotted on a Poincare plot 90 in the direction of line 96. For example, analysis module 14 may determine a distance in the direction of line 96 between the two plotted points most distant from line 92 in each direction.

Figure 5:
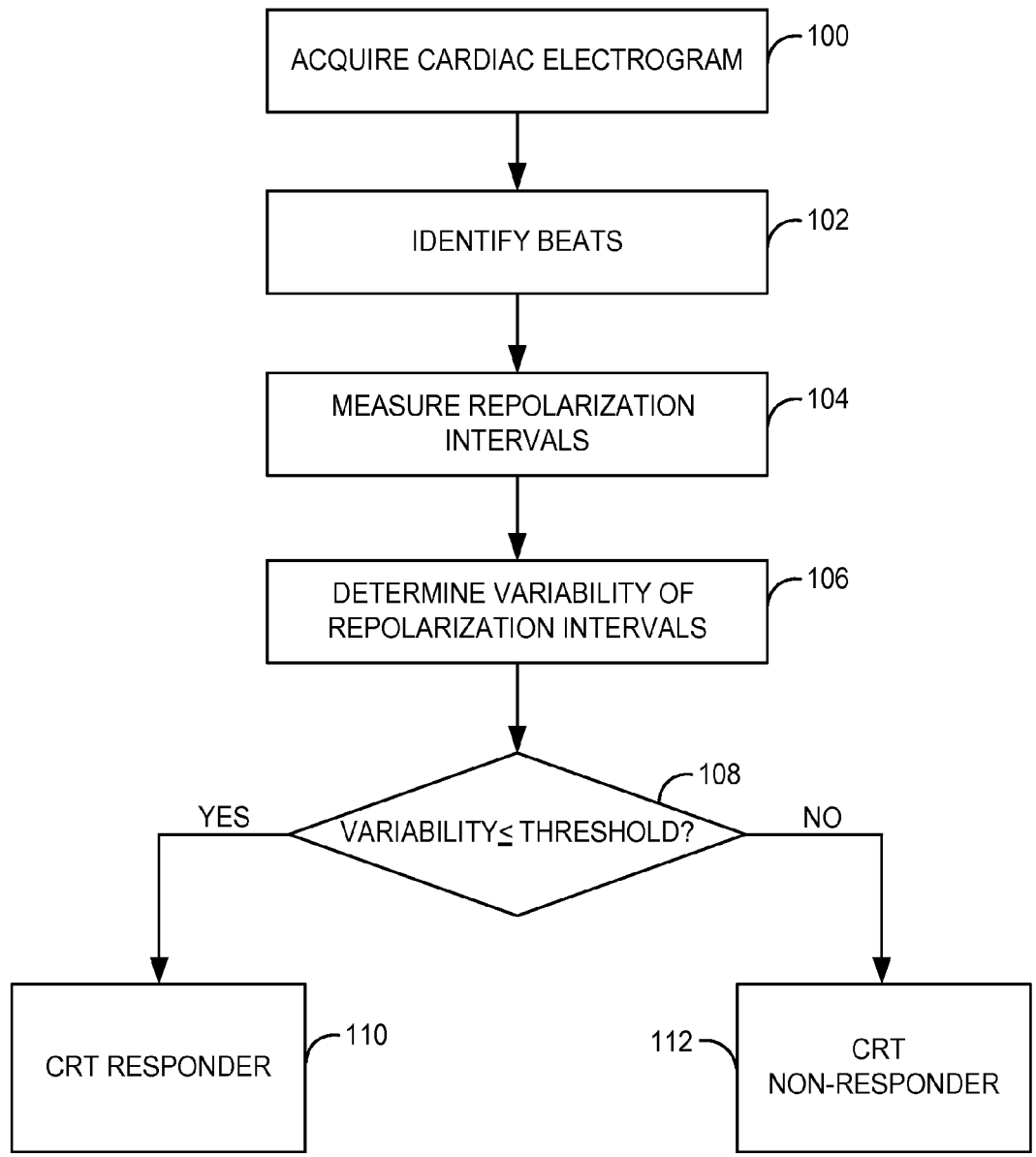
FIG. 5 is a flow diagram illustrating an example method for determining whether a patient will respond to CRT based on repolarization interval variability.

FIG. 5 is a flow diagram illustrating an example method for determining whether a patient will respond, e.g., is likely to respond or has a greater likelihood of responding, to CRT based on repolarization interval variability. The example method of FIG. 5 may be implemented by any system 10 described herein, or any other system, for determining whether a patient will respond to CRT.

According to the example method of FIG. 5, an acquisition module 12 acquires a cardiac electrogram, e.g., a digital, twelve-lead ECG (100). Analysis module 14 identifies beats 50 in the cardiac electrogram (102). For example, analysis module 14 may identify one or more fiducial features, e.g., R-wave and/or T-wave, of the cardiac cycle within the cardiac electrogram, and segment the cardiac electrogram into a plurality of consecutive beats 50 that each include one of each of the features.

For each of the plurality of consecutive beats 50, analysis module 14 measures a repolarization interval 70, e.g., QT interval or other ARI, using any of the techniques described herein (104). Analysis module 14 then determines the variability of the repolarization intervals 70, e.g., using any of the techniques described herein (106). For example, analysis module may determine the short-term, beat-to-beat variability of the repolarization intervals 70 using equation (1) and/or the Poincare plot techniques described with reference to FIGS. 4A and 4B. Analysis module 14 then determines whether the patient will respond to CRT based on the determined variability.

According to the example method of FIG. 5, analysis module 14 determines whether the patient will respond to CRT by comparing the determined variability of repolarization to a predetermined threshold (108). If the variability is less than or equal to (or less than) the threshold, the patient is classified as a CRT responder, e.g., is classified as being relatively likely to respond, or having a relatively high likelihood of responding, to CRT (110). If the variability is greater than (or greater than or equal to) the threshold, the patient is classified as a CRT non-responder, e.g., is classified as being relatively less likely to respond, or having a relatively lower likelihood of responding, to CRT (112). In this manner, analysis module 14 may classify a patient as either a CRT responder or CRT non-responder based on the determined variability of repolarization, e.g., based on a comparison of the variability to a predetermined threshold.

Although generally described herein with respect to examples in which the variability of repolarization is compared to a single threshold to determine whether a patient is classified as a CRT responder or a CRT non-responder, the techniques of this disclosure are not so limited. In some examples, a system 10, e.g., analysis module 14, may compare the variability of repolarization to a plurality of thresholds, and classify the patient as a CRT responder or a CRT non-responder based on the comparison of the variability to the plurality of thresholds.

For example, a system 10, e.g., analysis module 14, may compare the variability of repolarization to two thresholds, and classify the patient as a CRT responder or a CRT non-responder based on the comparison of the variability to the two thresholds. The two thresholds may include a first, lower threshold, and a second, higher threshold, that is greater than the first threshold. In such examples, the system may classify the patient as a CRT responder, e.g., as having a relatively higher likelihood of responding to CRT, when the repolarization variability is less than the first threshold. In such examples, the system may classify the patient as a CRT non-responder, e.g., as having a relatively lower likelihood of responding to CRT, when the repolarization variability is greater than the second threshold.

When the repolarization variability is between the first and second thresholds, i.e., greater than the first threshold, but less than the second threshold, the system may neither classify the patient as a CRT responder, nor as a CRT non-responder. The range between the first and second thresholds may define a "grey area" in that repolarization variability values within the range are not considered sufficiently associated with CRT response or non-response to classify a patient as a CRT responder or CRT non-responder. When the variability if between the first and second thresholds, the system may provide an indication, e.g., via user interface 18: that the patient cannot be classified as either a CRT responder or CRT non-responder, or that the patient's status as a CRT responder is indeterminate; that the repolarization variability is not sufficiently low to classify the patient as a CRT responder or sufficiently high to classify the patient as a CRT non-responder; or of the determined repolarization variability value.

In other examples, when the repolarization variability is within the range defined by the first and second thresholds, the system may classify the patient as either a CRT responder or CRT non-responder based on additional information, such as demographic information of the patient (e.g., age or gender), physical characteristics of the patient (e.g., obesity or other weight), or disease state (e.g., heart failure state). Depending on the clinical or experimental data used to determine the thresholds, e.g., characteristics of the test subjects or patients whose repolarization variability values were used to derive the threshold values, values within the range between the first and second thresholds may be more or less accurate in indicating the likelihood of CRT response for different populations of patients. In some examples, a single threshold may adequately distinguish between CRT responders and non-responders, if the test subject or patient group used to derive the threshold was sufficiently varied, e.g., in terms of age, gender, weight, and/or disease state.

The one or more predetermined thresholds used for any of the techniques described herein may be programmable by a user and/or determined based on experimental observation of repolarization interval variabilities of other subjects or patients who were CRT responders and CRT non-responders. In some examples, memory 16 may store a plurality of predetermined thresholds, and analysis module 14 may select one of the thresholds for a particular patient based on, for example, demographic information of the patient, physical characteristics of the patient, or disease, e.g., heart failure, state.

Figure 6:
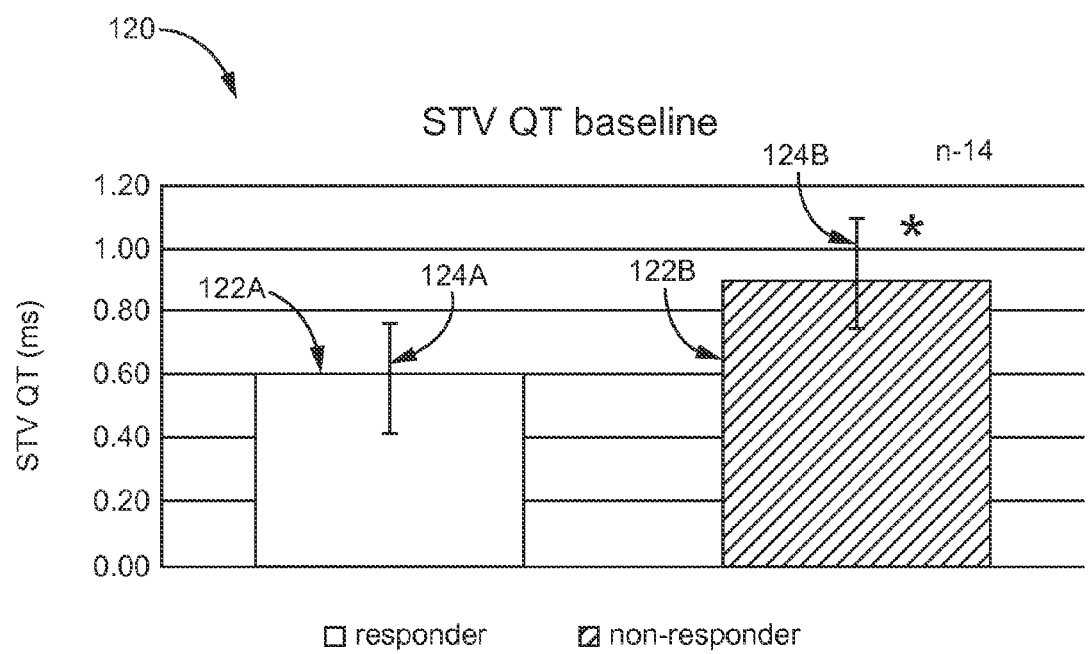
FIG. 6 is a bar graph of experimental data comparatively illustrating repolarization interval variability for CRT responders and CRT non-responders.

FIG. 6 is a bar graph 120 of experimental data comparatively illustrating repolarization interval variability for CRT responders and CRT non-responders. Bar graph 120 illustrates the results of study of fourteen heart failure patients. The results suggest that short-term, beat-to-beat variability of cardiac repolarization, such as short-term variability of the QT interval (STVQT) can accurately distinguish CRT responders from CRT non-responders.

Fourteen heart failure patients (79% male, 64% ischemic, mean LVEF 25±8 were prospectively included in the study prior to implantation of an IMD to deliver CRT. For each of the patients, a digital, twelve lead ECG was recorded with a sample frequency of 1200 Hz. For each patient, thirty-one consecutive beats were identified and aligned semi-automatically. Subsequently, a baseline (pre-implantation) value of STVQT was automatically calculated for each patient using techniques substantially as described herein, e.g., equation (1) and/or a Poincare plot. Additionally, for each patient, a baseline LVESV was measured by echocardiography as a measure of baseline cardiac function.

After implantation of the IMD and delivery of CRT, each of the fourteen patients was evaluated after at least six months to determine whether the patient was a CRT responder or a CRT non-responder. In particular, for each patient, post-CRT LVESV was measured by echocardiography. Patients whose LVESV decreased by at least 15% relative to the baseline LVESV were considered CRT responders, while those LVESV did not decrease by at least 15% were considered CRT non-responders.

Bar graph 120 of FIG. 6 illustrates the difference in STVQT for the patients classified as CRT responders relative to those considered CRT non-responders. In particular, bar 122A and bar 122B illustrate the mean STVQTs for CRT responders and CRT non-responders, respectively. Line 124A and line 124B illustrate the standard deviation of STVQT for CRT responders and CRT non-responders, respectively. As illustrated in FIG. 6, STVQT is significantly higher in the CRT non-responder group. The relative means and standard deviations of STVQT for CRT responders and CRT non-responders suggests that short-term variability of repolarization intervals may be an effective biomarker for classifying a particular patient as either a CRT responder or a CRT non-responder.

Figure 7:
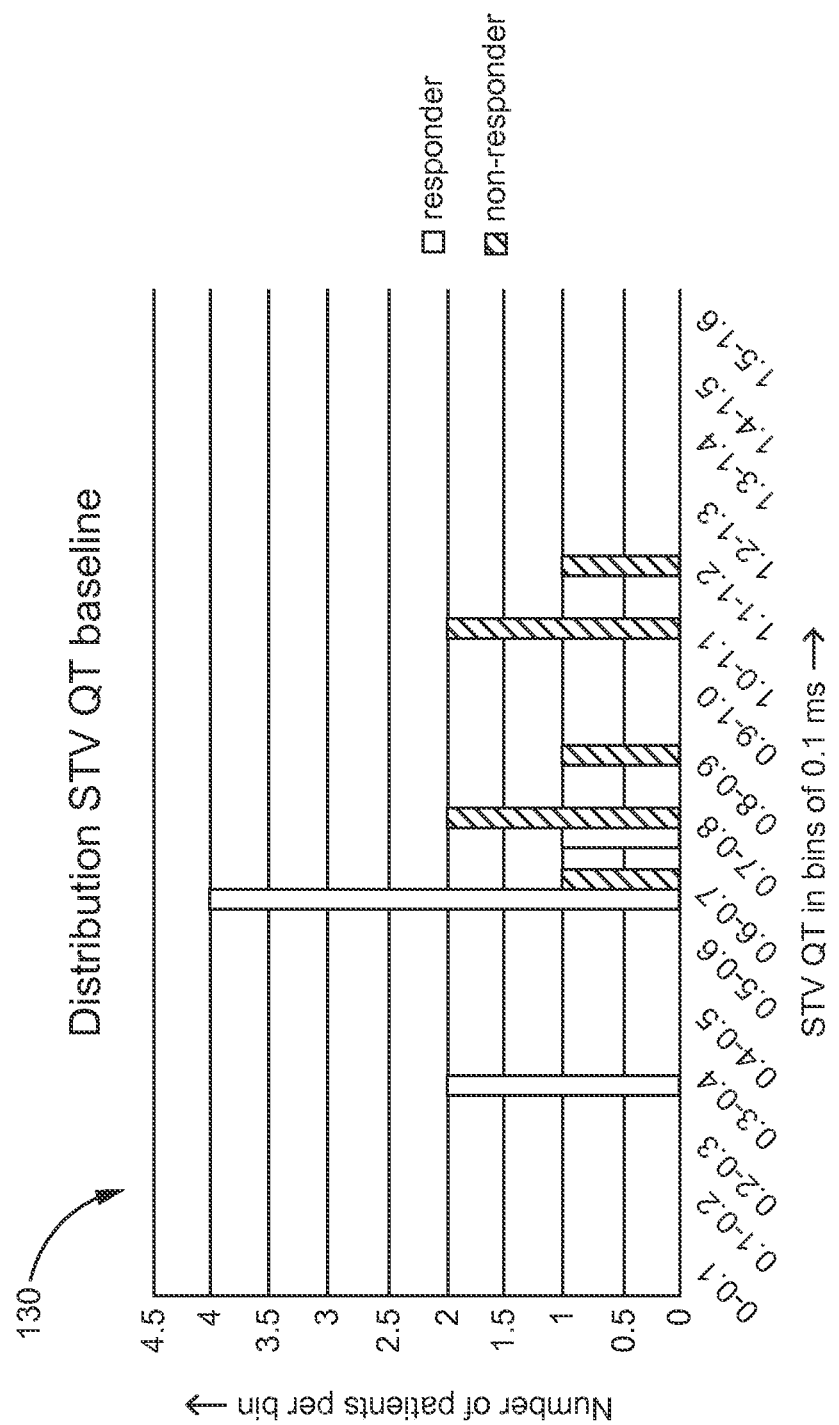
FIG. 7 is a histogram of experimental data comparatively illustrating repolarization interval variability for CRT responders and CRT non-responders.

FIG. 7 is a histogram 130 of experimental data, and particularly the STVQT data of the fourteen patient study discussed above with respect to FIG. 6, comparatively illustrating repolarization interval variability for CRT responders and CRT non-responders. In histogram 130, each bin represents a range of STVQT values, and the vertical axis represents the number of patients in each range. As illustrated by FIG. 7, there is only overlap between CRT responders and CRT non-responders with the STVQT range of 0.6 ms-0.8 ms. Additionally, there is only overlap of the categories in one patient, as only one CRT non-responder has a lower STVQT than one CRT responder (and conversely only one CRT responder has a higher STVQT than one CRT non-responder. Accordingly, histogram 130 of FIG. 7 suggests that repolarization interval variability has high sensitivity and specificity, and therefore high predictive value, for predicting whether a patient will respond to CRT. Preliminarily, the study suggests that repolarization interval variability has a predictive value of approximately 80%.

Hearts of CRT non-responders may be more diseased than those of CRT responders. In particular, there may be more structural, and associated electrical, remodeling of the heart of CRT non-responders relative to CRT responders. As a result of the electrical remodeling of the heart, CRT non-responders may lack repolarization reserve to respond to challenges to the heart. The lack of repolarization reserve in CRT non-responders may be evident in greater repolarization variability.

In some examples, the techniques of disclosure may include delivering a challenge to the heart prior to and/or during acquisition of the cardiac electrogram for determining whether the patient will respond to CRT. The challenge may be, for example, directing the patient to exercise or otherwise experience physical exertion, deliver of a pharmacological substance, delivery of cardiac pacing, or any other challenge which may cause the heart rate of the patient to increase and/or vary.

As described above, the techniques of this disclosure may facilitate identification of a particular patient as a CRT responder or CRT non-responder prior to implantation of an IMD to deliver CRT. Accordingly, repolarization variability may assist a clinician in the decision making for CRT implantation.

Various examples have been described. These and other examples are within the scope of the following claims.

The invention claimed is:

1. A system for determining whether a patient will respond to cardiac resynchronization therapy (CRT), the system comprising:
   an acquisition module configured to acquire a cardiac electrogram of the patient; and
   an analysis module configured to:
      identify a plurality of consecutive cardiac beats within the cardiac electrogram,
      for each of the consecutive cardiac beats, measure a repolarization interval between depolarization and repolarization, and
      determine a variability of the measured repolarization intervals, wherein the variability of the measured repolarization intervals indicates a likelihood that the patient will respond to CRT.

2. The system of claim 1, wherein the cardiac electrogram comprises an electrocardiogram sensed by a plurality of electrodes configured to be placed on a surface of the patient.

3. The system of claim 1, wherein the analysis module is configured to, for each of the consecutive cardiac beats, measure a QT interval as the repolarization interval, and determine a variability of the measured QT intervals, wherein the variability of the measured QT intervals indicates the likelihood that the patient will respond to CRT.

4. The system of claim 1, wherein the analysis module is configured to determine a beat-to-beat variability of the measured repolarization intervals, wherein the beat-to-beat variability of the measured repolarization intervals indicates the likelihood that the patient will respond to CRT.

5. The system of claim 4, wherein the analysis module is configured to generate a Poincare plot of the consecutive repolarization intervals, and determine the beat-to-beat variability of the measured repolarization intervals based on the Poincare plot.

6. The system of claim 1, wherein the analysis module is configured to:
   compare the determined variability of the measured repolarization intervals to a predetermined threshold;
   classify the patient as a responder to CRT if the determined variability is less than the threshold; and
   classify the patient as a non-responder to CRT if the determined variability is greater than the threshold.

7. The system of claim 1, wherein the analysis module is configured to:
   compare the determined variability of the measured repolarization intervals to a first threshold and a second threshold, wherein the second threshold is greater than the first threshold;
   classify the patient as a responder to CRT if the determined variability is less than the first threshold; and
   classify the patient as a non-responder to CRT if the determined variability is greater than the second threshold.

8. The system of claim 1, further comprising a user interface, wherein the analysis module is configured to provide an indication of whether the patient will respond to CRT via the user interface based on the determined variability of the measured repolarization intervals.

9. The system of claim 1, further comprising an electrocardiogram device and a computing device, wherein the computing device comprises the acquisition module and the analysis module, and the acquisition module is configured to acquire an electrocardiogram sensed by the electrocardiogram device via a plurality of electrodes on a surface of the patient as the cardiac electrogram.

10. A method for determining whether a patient will respond to cardiac resynchronization therapy (CRT), the method comprising:
   acquiring a cardiac electrogram of the patient;
   identifying a plurality of consecutive cardiac beats within the cardiac electrogram;
   for each of the consecutive cardiac beats, measuring a repolarization interval between depolarization and repolarization; and
   determining a variability of the measured repolarization intervals, wherein the variability of the measured repolarization intervals indicates a likelihood that the patient will respond to CRT.

11. The method of claim 10, wherein the cardiac electrogram comprises an electrocardiogram sensed by a plurality of electrodes on a surface of the patient.

12. The method of claim 10,
   wherein measuring the repolarization intervals comprises, for each of the consecutive cardiac beats, measuring a QT interval, and
   wherein determining the variability of the measured repolarization intervals comprises determining the variability of the measured QT intervals, wherein the variability of the measured QT intervals indicates the likelihood that the patient will respond to CRT.

13. The method of claim 10, wherein determining the variability of the measured repolarization intervals comprises determining a beat-to-beat variability of the measured repolarization intervals, wherein the beat-to-beat variability of the measured repolarization intervals indicates the likelihood that the patient will respond to CRT.

14. The method of claim 13, wherein determining the beat-to-beat variability of the measured repolarization intervals comprises:
- generating a Poincare plot of the consecutive repolarization intervals; and
- determining the beat-to-beat variability of the measured repolarization intervals based on the Poincare plot.

15. The method of claim 10, further comprising:
- comparing the determined variability of the measured repolarization intervals to a predetermined threshold;
- classifying the patient as a responder to CRT if the determined variability is less than the threshold; and
- classifying the patient as a non-responder to CRT if the determined variability is greater than the threshold.

16. The method of claim 10, further comprising:
- comparing the determined variability of the measured repolarization intervals to a first threshold and a second threshold, wherein the second threshold is greater than the first threshold;
- classifying the patient as a responder to CRT if the determined variability is less than the first threshold; and
- classifying the patient as a non-responder to CRT if the determined variability is greater than the second threshold.

17. The method of claim 10, further comprising providing an indication of whether the patient will respond to CRT via a user interface based on the determined variability of the measured repolarization intervals.

18. A system for determining whether a patient will respond to cardiac resynchronization therapy (CRT), the system comprising:
- means for acquiring a cardiac electrogram of the patient;
- means for identifying a plurality of consecutive cardiac beats within the cardiac electrogram;
- for each of the consecutive cardiac beats, means for measuring a repolarization interval between depolarization and repolarization; and
- means for determining a variability of the measured repolarization intervals, wherein the variability of the measured repolarization intervals indicates a likelihood that the patient will respond to CRT.

19. The system of claim 18,
- wherein the means for measuring the repolarization intervals comprises, for each of the consecutive cardiac beats, means for measuring a QT interval, and
- wherein the means for determining the variability of the measured repolarization intervals comprises means for determining the variability of the measured QT intervals, wherein the variability of the measured QT intervals indicates the likelihood that the patient will respond to CRT.

20. The system of claim 18, wherein the means for determining the variability of the measured repolarization intervals comprises means for determining a beat-to-beat variability of the measured repolarization intervals, wherein the beat-to-beat variability of the measured repolarization intervals indicates the likelihood that the patient will respond to CRT.

21. The system of claim 18, further comprising:
- means for comparing the determined variability of the measured repolarization intervals to a predetermined threshold;
- means for classifying the patient as a responder to CRT if the determined variability is less than the threshold; and
- means for classifying the patient as a non-responder to CRT if the determined variability is greater than the threshold.

22. The system of claim 18, further comprising:
- means for comparing the determined variability of the measured repolarization intervals to a first threshold and a second threshold, wherein the second threshold is greater than the first threshold;
- means for classifying the patient as a responder to CRT if the determined variability is less than the first threshold; and
- means for classifying the patient as a non-responder to CRT if the determined variability is greater than the second threshold.

23. A non-transitory computer-readable storage medium comprising program instructions that, when executed by one or more processors of a system for determining whether a patient will respond to cardiac resynchronization therapy (CRT), cause the processors to:
- acquire a cardiac electrogram of the patient;
- identify a plurality of consecutive cardiac beats within the cardiac electrogram;
- for each of the consecutive cardiac beats, measure a repolarization interval between depolarization and repolarization; and
- determine a variability of the measured repolarization intervals, wherein the variability of the measured repolarization intervals indicates a likelihood that the patient will respond to CRT.

* * * * *